(12) United States Patent
Van Hoorn et al.

(10) Patent No.: US 9,333,188 B2
(45) Date of Patent: May 10, 2016

(54) COMPOSITION AND METHOD FOR IMPROVING SURVIVAL OF BEE COLONIES

(71) Applicant: Science in Water B.V., Abcoude (NL)

(72) Inventors: Maarten Van Hoorn, Abcoude (NL); Rik Ter Horst, Abcoude (NL)

(73) Assignee: Science in Water B.V., Abcoude (NL)

( * ) Notice: Subject to any disclaimer, the term of this patent is extended or adjusted under 35 U.S.C. 154(b) by 0 days.

(21) Appl. No.: 13/963,763

(22) Filed: Aug. 9, 2013

(65) Prior Publication Data

US 2014/0045407 A1 Feb. 13, 2014

(30) Foreign Application Priority Data

Aug. 9, 2012 (NL) ................................... 2009308

(51) Int. Cl.

| | |
|---|---|
| *A01K 53/00* | (2006.01) |
| *A61K 31/295* | (2006.01) |
| *A61K 31/70* | (2006.01) |
| *A23L 1/304* | (2006.01) |
| *A23K 1/175* | (2006.01) |
| *A23K 1/18* | (2006.01) |
| *A61K 35/10* | (2015.01) |
| *A23K 1/06* | (2006.01) |
| *A23K 1/14* | (2006.01) |
| *A23K 1/16* | (2006.01) |

(52) U.S. Cl.
CPC .................. *A61K 31/295* (2013.01); *A23K 1/06* (2013.01); *A23K 1/146* (2013.01); *A23K 1/1603* (2013.01); *A23K 1/1612* (2013.01); *A23K 1/1631* (2013.01); *A23K 1/1643* (2013.01); *A23K 1/175* (2013.01); *A23K 1/1758* (2013.01); *A23K 1/1873* (2013.01); *A23L 1/3045* (2013.01); *A61K 31/70* (2013.01); *A61K 35/10* (2013.01)

(58) Field of Classification Search
CPC ..... A01K 47/00; A01K 53/00; A61K 31/295; A61K 31/70; A61K 35/10; A23L 1/3045; A23K 1/1758; A23K 1/1873; A23K 1/06; A23K 1/146; A23K 1/1603; A23K 1/1612; A23K 1/1631; A23K 1/1643; A23K 1/175
USPC .................................. 449/1, 2; 43/124, 132.1
IPC ............................................ A01K 47/00, 53/00
See application file for complete search history.

(56) References Cited

U.S. PATENT DOCUMENTS

| | | | |
|---|---|---|---|
| 5,023,359 A * | 6/1991 | Bounias et al. | ................ 556/114 |
| 2011/0171324 A1 | 7/2011 | Clemente | |
| 2014/0212520 A1 * | 7/2014 | Del Vecchio | .................. 424/744 |

FOREIGN PATENT DOCUMENTS

| | | | | |
|---|---|---|---|---|
| JP | 04079829 A | * | 3/1992 | .............. A01M 1/00 |
| WO | 2005110384 A2 | | 11/2005 | |

OTHER PUBLICATIONS

Bounias et al., "Varroa jacobsoni control by feeding honey bees with organic cupric salts".*
English-language Abstract of JP 04079829A.*
Kuterbach et al., Iron-Containing Cells in the Honey-Bee (*Apis mellifera*), J. exp. Biol. 126, 389-401 (1986).*
Search Report and Written Opinion of European Patent Office in application NL2009308.

* cited by examiner

*Primary Examiner* — Lisa Tsang
(74) *Attorney, Agent, or Firm* — Kinney & Lange, P.A.

(57) ABSTRACT

The invention is in the field of bee keeping; in particular the invention relates to a composition and a method for improving winter survival of individual bees and/or bee colonies and/or for preventing colony collapse. Research at Science in Water has led to the discovery that administering iron(II) to bees under certain conditions can reduce instances of winter mortality and CCD.

10 Claims, No Drawings

COMPOSITION AND METHOD FOR IMPROVING SURVIVAL OF BEE COLONIES

The invention is in the field of bee keeping; in particular the invention relates to a composition and a method for improving winter survival of individual bees and/or bee colonies and/or for preventing colony collapse.

Beekeepers worldwide have reported high rates of attrition in their bee colonies over recent years as a result of winter mortality and so called colony collapse disorder. Colony collapse disorder (CCD) is a phenomenon whereby bees from a beehive abruptly "disappear", i.e. suddenly and permanently leave the beehive.

High winter mortality and cases of CCD mean that beekeepers have a lower capacity to pollinate crops (in particular for cultivation of fruit, vegetables and certain agricultural crops) and to produce honey. Consequently bee keepers lose money and/or incur costs, such as related to replacing the bees, additional feeding, the use of pollen substitutes, broad spectrum food supplements, acarides and other pesticides.

Researchers in the United States have identified 61 causes that could lead to winter mortality. Whilst the exact cause remains unknown, presence of the Varroa mite in bee colonies is thought to play an important role. Causes of colony collapse disorder are less well understood. The fungus Nosema Ceranae has been implicated, but evidence is lacking.

In the absence of concrete understanding of the causes of winter mortality and CCD, there are as yet no solutions for their prevention. There are means and methods designed to limit the extent of Varroa mite infestation. Examples include the use of formic acid, oxalic acid and thymol, however there is some doubt in the field as to whether their use reduces instances of winter mortality and CCD. Interest has recently shifted to identifying if viruses transmitted by the mites could be a cause of winter mortality rather than the Varroa mites themselves.

It is an object of the invention to provide a composition and method for improving winter survival of individual bees and/or bee colonies and/or for preventing colony collapse.

In a first aspect, the invention relates to an aqueous composition for administration to bees for improving winter survival of individual bees and/or bee colonies, and/or for preventing colony collapse, wherein the aqueous composition comprises in combination (i) one or more iron(II) compound(s), (ii) one or more iron(II) chelating ligand(s), and (iii) one or more sugar(s).

Research at Science in Water has shown that iron deficiency may be an important contributor to winter mortality and CCD and have demonstrated that administration of the composition of the invention to bees reduces instances thereof.

It has also been noted that administration of such a composition to bees to which Varroa mites have attached causes the Varroa mites to fall-off. Since the bees no longer have to support the Varroa mites, they have improved vitality leading to increased productivity (in terms of food and pollen collection) and to better self-care (grooming).

With regards to the individual components of the composition:

The one or more iron(II) compounds are provided as food supplements. In principle any water-soluble iron(II) compound may be used in making up the composition provided the counter ion is non-toxic for bees at concentrations used in practice. Preferred iron(II) compounds are identified below.

Chelating ligands ensure the solubility of iron(II) compound in aqueous solution, prevent it from precipitating as insoluble iron hydroxide and maintain the iron in its +2 oxidation state. Only iron(II) can be metabolised by bees. Chelating ligands further serve to facilitate uptake and metabolisation of the iron(II).

Chelating ligands are compounds that can coordinate to a metal core through multiple functional groups, i.e. they are multidentate. Typically coordination is via functional groups of the chelating ligand that are able to donate electrons to the metal. As an example, humic and fulvic acids are chelating ligands that are able to complex iron(II) via carboxylate or phenolate groups. Metals bound by ligands are commonly referred to as coordination complexes. Wherein these ligands are chelating ligands the coordination complex is stabilised by the so-called chelate effect.

Sugar encourages bees to ingest the composition, thus avoiding the need for more complicated and/or convoluted administration strategies which would likely be more costly and less reliable. The sugars may be mono-, di- or polysaccharides. A person of skill in the art is familiar with suitable sugars.

The one or more water soluble iron(II) compound(s) is/are preferably selected from a group comprising iron(II) fumarate, iron(II) lactate, iron(II) gluconate, and combinations thereof.

Advantages of the above identified iron(II) compounds are that they are readily and cheaply available; there is wide experience of using these compounds to treat iron deficiency in the medical sector, and; fumaric, lactic and gluconic acids are weak acids that do not adversely affect the bees.

The one or more iron(II) chelating ligand(s) is/are preferably selected from a group comprising humic acids, fulvic acids and combinations thereof.

Humic and fulvic acids are classes of complex acids formed by the microbial degradation and modification of dead plant matter. These acids comprise multiple phenolic and carboxylic acid groups through which they are able to chelate metal ions such as iron(II). They are also present in high concentrations in vinasse (see below). These acids are cheaply and readily available and are not harmful to bees, though an overdosis is possible depending on the circumstances, the condition of the bees, etc.

The one or more sugar(s) is/are preferably selected from a group comprising sucrose, fructose, glucose, galactose, mannose, xylitol, sorbitol and combinations thereof.

The pH of the aqueous composition is preferably less than 6. In general bees live in a slightly acid environment; the pH of honey for example is in the range of 4-5. The pH of the composition is not particularly critical, but a value below 6 is advantageous both for maintaining the iron(II) in solution and for facilitating uptake of iron in the composition by the bees.

In a preferred embodiment, the aqueous composition comprises vinasse.

Vinasse is a byproduct of the fermentation industry known to a person of skill in the art. Sugarcane or sugar beet is processed to produce crystalline sugar, pulp and molasses. The latter are further processed by fermentation to ethanol, or other products. After the removal of the desired product the remaining material is called vinasse. Vinasse is sold after a partial dehydration and usually has a viscosity comparable to molasses. Commercially offered vinasse comes either from sugar cane and is called cane-vinasse or from sugar beet and is called beet-vinasse. Vinasse is rich in humic and fulvic acids (approx. 50% m/m) and also contains potassium, phosphate, and indigestible sugars.

In a preferred embodiment, the aqueous composition of the invention comprises an iron(II) compound, preferably iron (II) fumarate, and vinasse wherein at least a portion of the one or more iron(II) chelating ligand(s) and one or more sugar(s) are from vinasse.

Vinasse is also readily and cheaply available and has been shown not to substantially affect the bees when added in low dosages. In the composition the vinasse preferably has a dilution in the range of 1:10 to 1:1000, preferably 1:100 relative to commercially available vinasse.

In a preferred embodiment the composition further comprises one or more of: an antioxidant such as ascorbic acid, sugars, protein-rich food supplements, vitamins, essential minerals, essential oils. Such are beneficial for maintaining the health of the bees throughout the year and in particular during the winter. Essential oils include thymol, lemongrass oil, eucalyptus oil and spearmint oil. Such are able to chelate minerals and can facilitate their uptake and metabolism by bees.

Ultimately the composition of the invention such as including one or more of: an antioxidant such as ascorbic acid, sugars, protein-rich food supplements, vitamins, essential minerals increases the probability that the bees will live long lives. Thus a favourable ratio of old to young bees may be maintained ensuring that e.g. sufficient pollen and nectar can be gathered to support development of the next generation.

In a second aspect, the invention relates to a method for improving winter survival of individual bees and/or bee colonies, and/or preventing colony collapse, wherein the method comprises administering 0.5 to 600 millimoles, preferably 0.5 to 120 millimoles, most preferably 5 to 60 millimoles of iron(II), per 5 kg of bees over a period of at least 3 weeks, preferably 6-12 weeks, most preferably 8-12 weeks, at least ending during the wintering period. Wintering is a term known to a person of skill in the art relating to the period during which the beehives must be made ready for winter. Such can be estimated for a particular location based on past experience.

The total dose is preferably administered as approximately equal portions thereof 1-7 times per week, preferably 1-3 times per week.

In a preferred embodiment, one or more of the following are administered in combination with the iron(II) compound over the same period: (i) humic and/or fulvic acid(s), (ii) vinasse, (iii) ascorbic acid, (iv) protein-rich food supplements, (v) vitamins, (vi) essential minerals (vii) sugars, (viii) essential oils.

In a preferred embodiment administration comprises providing the iron(II) compound(s) in combination with any additional compounds, such as (i) humic and/or fulvic acid(s), (ii) vinasse, (iii) ascorbic acid, (iv) protein-rich food supplements, (v) vitamins, (vi) essential minerals, (vii) essential oils, in the bee hive, preferably as a sugar solution, pattie or sugar dough thereof. The terms pattie and sugar dough are known to a person of skill in the art and relate to a protein containing dough and a mix of flour, sugar and water respectively.

By providing the iron(II) and any further compounds such as those identified in the previous paragraph in the bee hive, it can be ensured that only the resident bees take up the iron(II) allowing uptake to be monitored and/or controlled. Resident bees are bees belonging to the population of a particular hive including nurse bees and worker bees.

The invention will now be further elucidated through the following example (see Table 1) which is not to be interpreted as limiting of the invention.

EXAMPLE

In a trial, a number or beekeepers (16) used a solution of vinasse containing dissolved iron(II) fumarate with the goal of reducing instances of winter mortality and CCD. This solution was mixed with 100-200 ml of sugar syrup. The solution thus obtained was administered to bees with their feed. The quantities and results were as follows: A total of approximately 1,000 mg of iron(II) fumarate, or 333 mg Fe (i.e. 5.8 millimoles iron(II)) was administered per 5 kg of bees. This quantity was administered in small portions. The initial moments of the series administrations ranged from 5 August 2011 to 15 September 2011. The administration frequencies ranged from one time per week to one time per 3 days. If administration was started late in the season, administration was one time per 3 days to ensure that a consistent total amount of iron(II) fumarate was administered across the test populations. In control populations given only iron(II) fumarate the bees survived the winter, but in a very weak state. In a control populations given only pure vinasse the queens were dead within 14 days; these populations were then not viable and after the death of the queen, remaining bees in the population were merged with another population. In one case, the total amount of iron(II) fumarate and vinasse was added to 15 kg of sugar syrup. This emulsion was administered as a winter sugar, until the mixture was consumed. The bees survived the winter. Results are shown in Table 1. *At location 4, both iron(II) with vinasse and iron without vinasse were tried.

With reference to Table 1. After addition of iron(II) fumarate in combination with vinasse the bee populations of 13 of the 16 bee keepers survived the winter. At three locations (3, 6, 10) the populations did not survive the winter. At these locations there has been high winter mortality. In combination with iron(II) and vinasse, also formic acid (10) or oxalic acid (3, 6) were used. At these locations, control populations and populations given only vinasse also did not survive the winter.

At locations 2, 5, 11 bees given only vinasse did not survive the winter; those that received both iron(II) and vinasse did survive. The bottom row of Table 1 gives the average mortality rates. The total average mortality of all bee populations at all locations wherein the trial was performed was in range of 26-28%. In Almere-Haven (current average mortality 60%) the bees that received both iron(II) and vinasse survived the winter.

TABLE 1

| Place | Location | All hives | | | V + Fe(II) | | V—Fe(II) | | Control | |
|---|---|---|---|---|---|---|---|---|---|---|
| | | living | total | mortality % | living | total | living | total | living | total |
| Vorden | 2 | 4 | 5 | 20 | 1 | 1 | 0 | 1 | 1 | 1 |
| Wassenaar | 3 | 4 | 11 | 45 | 0 | 1 | 0 | 1 | 0 | 1 |
| Oegstgeest* | 4 | 5 | 8 | 37 | 1 | 1 | — | — | 3 | 6 |
| Volker | 5 | 2 | 7 | 71 | 1 | 1 | 0 | 1 | 1 | 1 |
| Gemert | 6 | 2 | 6 | 67 | 0 | 1 | 0 | 1 | 0 | 1 |
| Zandhuizen | 7 | 2 | 2 | 0 | — | — | 1 | 1 | 1 | 1 |

TABLE 1-continued

| Place | Location | All hives | | | V + Fe(II) | | V—Fe(II) | | Control | |
|---|---|---|---|---|---|---|---|---|---|---|
| | | living | total | mortality % | living | total | living | total | living | total |
| Veenendal | 8 | 8 | 13 | 24 | 1 | 1 | 1 | 1 | 0 | 1 |
| Soest | 9 | 6 | 6 | 0 | 5 | 5 | — | — | 1 | 1 |
| Wateren | 10 | 2 | 8 | 75 | 0 | 1 | 0 | 1 | 0 | 1 |
| Helmond | 11 | 15 | 24 | 33 | 2 | 2 | 0 | 2 | 0 | 1 |
| Eersel | 12 | 8 | 16 | 50 | 2 | 2 | 2 | 2 | 2 | 2 |
| Hattem | 13 | 8 | 8 | 0 | 1 | 1 | 1 | 1 | 1 | 1 |
| Almere-Haven | 14 | 4 | 6 | 33 | 2 | 2 | 2 | 2 | 0 | 1 |
| Leusden | 15 | 10 | 10 | 0 | 1 | 1 | 1 | 1 | 1 | 1 |
| Drachten | 19 | 23 | 23 | 0 | 15 | 15 | — | — | 1 | 1 |
| Bathmen | 20 | 10 | 10 | 0 | 1 | 1 | 1 | 1 | 1 | 1 |
| Total number of hives | | 113 | 163 | | 33 | 36 | 9 | 16 | 13 | 22 |
| Number of locations | | 16 | 16 | | 12 | 15 | 7 | 13 | 10 | 16 |
| Average mortality % | | | | 31 | | 8 | | 44 | | 41 |

The invention claimed is:

1. A method for improving winter survival of individual bees or bee colonies, or preventing colony collapse, wherein the method comprises administering a total dose in a range of 0.5 to 600 millimoles of an iron(II) compound, per 5 kilograms (kg) of bees over a period of at least 3 weeks, the administering ending during a wintering period.

2. The method according to claim 1 wherein the total dose is administered in approximately equal portions thereof.

3. The method according to claim 1, wherein one or more of the following are administered in combination with the iron(II) compound over the same period: (i) humic fulvic acid(s), (ii) vinasse, (iii) ascorbic acid, (iv) protein-rich food supplements, (v) vitamins, (vi) essential minerals, (vii) sugars, and (viii) essential oils.

4. The method according to claim 1, wherein the administering comprises providing the iron(II) compound in a bee hive.

5. The method according to claim 1, wherein the method comprises administering the total dose in a range of 0.5 to 120 millimoles of the iron(II) compound, per 5 kg of bees over the period of at least 3 weeks ending during the wintering period.

6. The method according to claim 1, wherein the method comprises administering the total dose in a range of 5 to 60 millimoles of the iron(II) compound, per 5 kg of bees over the period of at least 3 weeks ending during the wintering period.

7. The method according to claim 1, wherein the method comprises administering the total dose in the range of 0.5 to 600 millimoles of the iron(II) compound, per 5 kg of bees over a period of 6-12 weeks ending during the wintering period.

8. The method according to claim 1, wherein the method comprises administering the total dose in the range of 0.5 to 600 millimoles of the iron(II) compound, per 5 kg of bees over a period of 8-12 weeks ending during the wintering period.

9. The method according to claim 1, wherein the total dose is administered in approximately equal portions thereof 1-3 times per week.

10. The method according to claim 1, wherein the administering comprises providing the iron(II) compound in a bee hive as a sugar solution, patty or sugar dough thereof.

* * * * *